United States Patent [19]

Larsson et al.

[11] Patent Number: 5,001,062

[45] Date of Patent: Mar. 19, 1991

[54] ANTITHROMBOGENIC ARTICLE CONTAINING LYSOZYME AND HEPARIN ADSORBED ON A SUBSTRATE

[75] Inventors: Kåre V. Larsson, Bjärred; Sven E. Bergentz; Bengt L. T. Lindblad, both of Malmö, all of Sweden

[73] Assignee: Camurus AB, Malmö, Sweden

[21] Appl. No.: 275,108

[22] PCT Filed: May 22, 1987

[86] PCT No.: PCT/SE87/00257

§ 371 Date: Nov. 14, 1988

§ 102(e) Date: Nov. 14, 1988

[87] PCT Pub. No.: WO87/07156

PCT Pub. Date: Dec. 3, 1987

[30] Foreign Application Priority Data

May 27, 1986 [SE] Sweden ................................ 8602414

[51] Int. Cl.$^5$ .................... C12N 11/14; C12N 11/08; A61K 37/54; A61K 31/715

[52] U.S. Cl. .................................. 435/176; 424/94.61; 435/180; 435/181; 435/206; 514/56

[58] Field of Search ............... 435/174, 176, 177, 180, 435/181, 206; 424/94.61; 514/56

[56] References Cited

U.S. PATENT DOCUMENTS

| | | | |
|---|---|---|---|
| 3,617,344 | 11/1971 | Leininger et al. | 117/47 |
| 3,639,141 | 2/1972 | Dyck | 427/2 |
| 3,810,781 | 5/1974 | Eriksson et al. | 117/47 A |
| 4,416,992 | 11/1983 | Arena et al. | 435/176 |
| 4,600,652 | 7/1986 | Solomon et al. | 428/423.3 |
| 4,613,665 | 9/1986 | Larm | 536/20 |
| 4,642,242 | 2/1987 | Solomon et al. | 427/2 |
| 4,810,784 | 3/1989 | Larm | 536/20 |

FOREIGN PATENT DOCUMENTS

| | | |
|---|---|---|
| 0051354 | 5/1982 | European Pat. Off. |
| 365710 | 4/1974 | Sweden |
| 377277 | 6/1975 | Sweden |

OTHER PUBLICATIONS

Thrombos. Diathes. haemorrh. (Stuttg.), 1975, 34, 127–144, (Anthony M. Benis et al.), "Extracorporeal Model for Study of Factors Affecting Thrombus Formation".

Boschetti, et al., Journal of Chromatography, vol. 210, 1981, pp. 469–475.

Bychkov, et al., Chemical Abstracts, vol. 68, Abstract No. 18724C, 1968, p. 1785.

Primary Examiner—David M. Naff
Attorney, Agent, or Firm—Burns, Doane, Swecker & Mathis

[57] ABSTRACT

An article adapted for applications where there is contact with blood and especially in medical applications is prepared by adsorbing the enzyme, lysozyme or derivative thereof, onto a substrate and then adsorbing heparin or a heparin-based material to the enzyme. The substrate is preferably a metal or polymeric material.

41 Claims, No Drawings

ANTITHROMBOGENIC ARTICLE CONTAINING LYSOZYME AND HEPARIN ADSORBED ON A SUBSTRATE

TECHNICAL FIELD

The present invention relates to the field of heparinization of materials for the purpose of imparting thereto a heparin layer which inhibits in contact with blood the adhesion of thrombocytes and the adsorption of blood proteins. Thus, the article according to the invention is especially suited for applications where there is contact with blood, e.g. medical applications. It is true that the methodology of heparinizing a material for the above-mentioned purpose is previously known per se, but the present invention relates to a novel, alternative method of adhering the heparin to the substrate, via a special, novel type of a pre-adsorbed layer. In addition to the above-mentioned article the invention relates to a process for the preparation thereof as well as to the use of said article for medical applications.

BACKGROUND OF THE INVENTION

To accomplish blood compatibility for different materials in contact with blood one of the most important methods has been to heparinize the surface thereof. Thus, the heparin layer on the surface inhibits, as was mentioned above, the adhesion of thrombocytes and the adsorption of blood proteins. Furthermore, the heparin must be enzymatically active in the blood coagulation process, which calls for specific necessities as to molecular conformation and mobility relative to the surface.

Two main principles for the heparinization have previously been utilized. The first one is based on colloidal precipitation, e.g. through complex-formation between amphiphilic amines and heparin. The second one utilizes the possibility of covalently bonding the heparin to the surface. However, these known principles have some limitations which means that there is continuous research for alternative or improved methods for the heparinization.

SUMMARY OF THE INVENTION

The present invention relates to an alternative or improved technique for the heparinization of surfaces, which technique eliminates or at least reduces the limitations of the prior art while at the same time imparting thereto, at least for certain applications, additional advantageous properties which have not been obtainable by the previously utilized technique. More specifically we have found that a specific protein, viz. lysozyme, possesses unexpected affinity for heparin and gives an outstanding adhesion to different substrate surfaces. The unexpectedly good results which have been obtained by the protein according to the invention will be described more in detail below, but primarily it can be mentioned that a very good adhesion to metal surfaces has been obtained, which is material in which previously known methods have shown deficiencies.

Lysozyme is a protein that is present in low concentrations in blood. Already there is an interesting advantage since the invention is based on the utilization of a substance which is non-foreign to the human organism. In addition thereto another interesting property of lysozyme is its antimicrobial properties which impart to the novel heparinized surface an antimicrobial activity; a security factor in storage and handling.

More specifically the article according to the invention is characterized in that heparin or a heparin-based material is adhered or bonded to the substrate via a layer of lysozyme or a derivative thereof which is pre-adsorbed to said substrate.

As was indicated above the novel technique according to the invention has been shown to work especially well for metal surfaces, in which previously known heparinizing methods have shown limitations. However, the invention is also applicable to other substrates which are chosen per se in accordance with previously known techniques, i.e. primarily such substrates that have has previously been desired to heparinize for the purpose of imparting to the same improved properties in applications where there is contact with blood. Examples of such materials are polymeric materials and glass. As far as polymeric materials are concerned it should be noted that the present invention is especially interesting in connection with polymeric materials of the so called low energy type. Low energy type means polymeric materials that are not wetted by water but by organic solvents.

Concerning the term "lysozyme or derivatives thereof" it should be understood that of course the invention is not limited to the use of lysozyme per se, but it is also possible to choose any derivative thereof which gives the corresponding or similar properties. Such a choice may for instance depend on better solubility in the desired solvent for a derivative than for lysozyme per se. Examples of utilizable derivatives may include salts, such as the chloride salt. Moreover, the invention is of course intended to cover such cases where the lysozyme has been modified within the molecule at a position or site that does not have any direct connection with the effect of the invention, i.e., a modification that does not change the desired properties according to the present invention.

The same requisite concerning heparin is that heparin per se does not have to be utilized to obtain the desired effect. Thus, the expression "heparin-based material" is intended to cover those heparin compounds which give a corresponding or similar effect, reference in this context being made to the prior art which discloses numerous examples of heparin compounds for the purpose referred to. Thus, in this connection the invention does not differ from the prior art.

Those applications for which the article claimed is especially well suited are also selected in accordance with the prior art, and thus need not be described herein. However, certain improvements of the properties or additional advantageous properties are obtained by the present invention, medicinal uses or other applications will become even more apparent in the present invention than described in the prior art.

The process according to the invention is characterized by first contacting the substrate with a solution of lysozyme or the derivative thereof to form a lysozyme layer and then exposing the substrate with its lysozyme layer to a heparin or heparin-based solution to adhere or bond the heparin or the heparin-based material to said lysozyme layer.

As is often the case for surfaces which are to be coated, such surfaces have to be comparatively clean to obtain the desired result. This is true also in the present invention, especially in the case where the substrate is a metal. In such a case the surface should be very clean, and is comprised of metal or metal oxides. In the ideal case this means that the surface should be cleaned or purified in a so called plasma cleaner and immediately thereafter transferred into distilled water. Alternatively, a consecutive washing in lye, acid and distilled water is acceptable. For a plastic surface, especially a low energetic one, the material is cleaned in water with a detergent and then an organic solvent. Concerning other substrates in principle those cleaning methods which have previously been utilized in connection therewith are applicable.

After said cleaning of the substrate surface, if required, the substrate is contacted with the lysozyme solution, which is commonly a water solution or an aqueous solution. Distilled water is often preferred relative to a buffer solution. In order to obtain a lysozyme layer the solution should have a concentration of at least 0.1 percent by weight. The upper limit is not especially critical to accomplish the desired effect, but generally the concentration should not exceed 10 percent by weight, since otherwise viscosity effects will interfere with the process. An especially preferable range for the concentration of lysozyme or derivative thereof is 0.1-2 percent by weight.

The residence time of said stage of treatment should be at least 15 minutes, preferably about 20 minutes. Such a period is normally required to attain a plateau value for the adsorption of lysozyme. Once said plateau or maximum value has been attained there is normally no reason to further extend the residence time, which generally means that said residence or treatment time is within the range of 15-30 minutes.

After said treatment with the lysozyme solution the substrate should be rapidly rinsed in water and then directly exposed to a heparin solution or a heparin based solution. Thus, it has been discovered, especially in connection with metals, that drying should not or must not be performed between the two coating stages, in order to obtain the optimum effect.

Also the solution of heparin or heparin-based compound is preferably water-based. For adsorption reasons the heparin solution concentration should be above 0.05 percent by weight, especially above 0.1 percent by weight. In this case the upper limit is not especially critical, and any additional effect is negligible at a concentration value exceeding about 5 percent by weight. Therefore, a generic range is 0.05-5, especially 0.1-5, percent by weight. However, in many cases said concentration should not even exceed about 2 percent by weight, since the viscosity will cause interferences. Thus, the specially preferred range is 0.1-2 percent by weight. However, concerning the heparin treatment in principle all applications from the prior art can be utilized, i.e. said stage is principally performed per se in accordance with the guide-lines of the prior art in this field.

The exposure time of the heparin solution or the heparin based solution is generally at least 20 minutes, preferably about 30 minutes, and more preferably between 20-45 minutes.

After exposure to the heparin solution the substrate is rinsed in distilled water, whereupon it is allowed to dry or is dryed after draining the excess solution. By rinsing in distilled water before drying the amount of heparin can be reduced to a monomolecular layer. However, for most applications a certain surface excess of dissolved adsorbed heparin is preferred.

Both of the above-mentioned surface treatments are preferably performed at room temperature. A slightly bigger temperature can be utilized if desired, but generally the temperature should not exceed about 50° C., since structural changes may appear in the lysozyme.

Finally the invention relates to the use of the above-defined article or of an article prepared by the process defined above, for medical applications where there is contact with blood. It should be noted that of course the term "medical applications" should be interpreted in a broad meaning; the use is not specifically limited to therapeutical treatments only.

The invention will now be further described by means of the following non-limiting examples. The percentages used therein relate to percentages by weight unless otherwise specifically stated.

EXAMPLE 1

A commercially available lysozyme from poultry egg white was checked by gel electrophoresis to be free of other egg white proteins. The lysozyme was then desalted by dialysis. A solution of 0.5 percent by weight of lysozyme in distilled water was then prepared. Metal cannulae were submersed in a bath of said solution for 20 minutes. Said metal cannulae were pre-cleaned for 5 minutes in a so called plasma cleaner at an air pressure of 5 torr. They were taken from the bath, rinsed with distilled water and immediately transferred to a bath consisting of a 0.1% heparin solution in distilled water. After 30 minutes the cannulae were removed from the bath, rapidly rinsed with distilled water and allowed to dry in a sterile chamber at 30° C. In this example metal cannulae having a heparin coating adhered via a pre-adsorbed layer of lysozyme were obtained.

EXAMPLE 2

Catheters of polyethylene were washed in a one percent Triton X-100 solution and then in ethanol (96%). Said catheters were submersed in a 0.1% lysozyme solution in distilled water. After about 20 minutes they were placed in a bath of distilled water, whereupon they were further transferred to a 0.1% heparin solution in distilled water. After 30 minutes the catheters were washed and were then allowed to dry thus forming articles of the present invention.

CLINICAL INVESTIGATION OF HEPARINIZED STEEL TUBES ACCORDING TO THE INVENTION

Several methods have been utilized in order to determine thrombogenicity for artificial materials. A previously utilized method is one in which steel tubes are inserted into blood vessels and are incubated in the vessel. During incubation the coagulation system reacts by adsorbing proteins on the extraneous surface and adhesion of thrombocytes and possible thrombosis of the inserted tube occurs. From an experimental point of view said methodology is a good method to study the formation of thrombosis in arteries as well as in veins.

Lately methods which utilize labeled radisisotopes have been used for studies of thrombogenicity. However, to estimate the thrombogenicity of steel tubes the previously used technique with an intravascular insertion of the steel tube and determination of the weight differences before and after incubation is the best method for an optimum determination of the thrombogenicity of the material. Steel tubes having a diameter of 4 mm, a length of 25 mm and a thickness of 0.1 mm were heparinized in accordance with Example 1 above.

MATERIALS AND METHODS

Three sheep, weighing about 40 kg. were anesthetized with pentobarbital at an initial concentration continuously in fused at a rate of 30 mg/kg. Afterwards the pentobarbital was 7.5 mg/min. The sheep were intubated and respirator ventilated with 40% $O_2$. The respirator frequency was 20/min, volume 10 1/min. Both carotids were explored and opened by a small longitudinal incision and the 25 mm long steel tube, tapered and polished, was inserted. In carotid on one side there was inserted a heparinized tube and in the other side a non-heparinized tube. Between different incubation periods the sides were changed. After preliminary testing the incubation time was selected as being 15 minutes.

RESULTS 25 incubation periods were performed. In all these the thrombus weights were considerably less on the heparinized tube than on the non-heparinized one (32+4 mg as compared to 210+10 mg). In addition there were additional thrombus masses in the vessel in seven cases when the steel tube was removed. All these thrombus masses were in non-heparinized tubes and had weights of 96, 201, 143, 369, 374, 216 and 199 mg.

Statistical calculations when using the student's paired t-test gave a t-value of t=9.20, df 25, reflecting a considerably significant reduction of thrombogenicity in the heparinized tubes.

We claim:

1. An antithrombogenic article consisting essentially of a substrate, an enzyme selected from the group consisting of lysozyme, a lysozyme derivative and a mixture thereof, which enzyme is preadsorbed directly to said substrate to form an enzyme layer, and an antithrombotic compound, selected from the group consisting of heparin, a heparin-based material and a mixture thereof, said antithrombotic compound being adhered to said substrate by adsorption to said enzyme layer.

2. An article according to claim 1, wherein the substrate is a metal.

3. An article according to claim 1, wherein the substrate is a polymeric material which is not wetted by water but by an organic solvent.

4. An article according to claim 1, wherein said antithrombotic compound is heparin.

5. An article according to claim 1, wherein said antithrombotic compound is a heparin-based compound.

6. An article according to claim 1, wherein said enzyme is lysozyme.

7. An article according to claim 1, wherein said enzyme is a lysozyme derivative.

8. A process for the preparation of an antithrombogenic article, said process consisting essentially of contacting a cleaned substrate with a solution comprising an enzyme selected from the group consisting of lysozyme, a lysozyme derivative and a mixture thereof, which enzyme is preadsorbed directly to said substrate to form an enzyme layer and exposing the substrate containing the enzyme layer to a solution containing an antithrombotic compound selected from the group consisting of heparin, a heparin-based material and a mixture thereof, to adsorb said antithrombotic compound to the enzyme layer.

9. A process according to claim 8, further comprising the step of rinsing with distilled water after forming the enzyme layer.

10. A process according to claim 8, wherein said solution containing an antithrombotic compound is an aqueous solution.

11. A process according to claim 8, wherein the concentration of enzyme in solution is between 0.1 to 10 percent by weight.

12. A process according to claim 11, wherein the concentration of enzyme in solution is between 0.1 to 2 percent by weight.

13. A process according to claim 8, wherein the concentration of said antithrombotic compound in solution is between 0.05 to 5.0 percent by weight.

14. A process according to claim 13, wherein the concentration of said antithrombotic compound in solution is between 0.1 to 2 percent by weight.

15. A process according to claim 8, wherein said enzyme solution is contacted with the substrate for at least 15 minutes.

16. A process according to claim 15, wherein said enzyme solution is contacted with the substrate for a period between 15 to 30 minutes.

17. A process according to claim 8, wherein the exposure to the antithrombotic compound solution is for a period of at least 20 minutes.

18. A process according to claim 17, wherein the exposure to the antithrombotic compound solution is for a period between 20 to 45 minutes.

19. A process according to claim 8, wherein said enzyme layer remains wet before exposure to said antithrombotic compound solution.

20. A process according to claim 13, wherein said enzyme solution is contacted with the substrate for at least 15 minutes.

21. A process according to claim 20, wherein said enzyme solution is contacted with the substrate for a period between 15 to 30 minutes.

22. A process according to claim 11, wherein the exposure to the antithrombotic compound solution is for a period of at least 20 minutes.

23. A process according to claim 22, wherein the exposure to the antithrombotic compound solution is for a period between 20 to 45 minutes.

24. A process according to claim 13, wherein the exposure to the antithrombotic compound solution is for a period of at least 20 minutes.

25. A process according to claim 24, wherein the exposure to the antithrombotic compound solution is for a period between 20 to 45 minutes.

26. A process according to claim 15, wherein the exposure to the antithrombotic compound solution is for a period of at least 20 minutes.

27. A process according to claim 26, wherein the exposure to the antithrombotic compound solution is for a period between 20 to 45 minutes.

28. A process according to claim 11, wherein said enzyme layer remains wet before exposure to said antithrombotic compound solution.

29. A process according to claim 13, wherein said enzyme layer remains wet before exposure to said antithrombotic compound solution.

30. A process according to claim 15, wherein said enzyme layer remains wet before exposure to said antithrombotic compound solution.

31. A process according to claim 17, wherein said enzyme layer remains wet before exposure to said antithrombotic compound solution.

32. A process for the preparation of an antithrombogenic article said process consisting essentially of first contacting a cleaned metal substrate with a solution containing an enzyme selected from the group consisting of lysozyme, a lysozyme derivative and a mixture thereof, which enzyme is preadsorbed directly to said substrate to form an enzyme layer and exposing the substrate with its enzyme layer to a solution containing an antithrombotic compound selected from the group consisting of heparin, a heparin-based material and a mixture thereof, to adsorb the antithrombotic compound to the enzyme layer.

33. A process according to claim 32, further comprising the step of rinsing the enzyme layer with distilled water prior to exposing the enzyme layer to the solution containing the antithrombotic compound.

34. A process according to claim 32, wherein said solution containing an antithrombotic compound is an aqueous solution.

35. A process according to claim 32, wherein said enzyme solution is contacted with the substrate for at least 15 minutes.

36. A process according to claim 35, wherein said enzyme solution is contacted with the substrate for a period between 15 to 30 minutes.

37. A process for the preparation of an article said process consisting essentially of first contacting a cleaned polymeric substrate with a solution containing an enzyme selected from the group consisting of lysozyme, a lysozyme derivative and a mixture thereof, which enzyme is preadsorbed directly to said substrate to form an enzyme layer and exposing the substrate with its enzyme layer to a solution containing an antithrombotic compound selected from the group consisting of heparin, a heparin-based material and a mixture thereof, to adsorb the antithrombotic compound to the enzyme layer.

38. A process according to claim 37, further comprising the step of rinsing the enzyme layer with distilled water prior to exposing the layer to the solution containing the antithrombotic compound.

39. A process according to claim 37, wherein said solution containing the antithrombotic compound is an aqueous solution.

40. A process according to claim 37, wherein the concentration of said antithrombotic compound in solution is between 0.05 to 5.0 percent by weight.

41. A process according to claim 40, wherein the concentration of said antithrombotic compound in solution is between 0.1 to 2 percent by weight.

* * * * *